United States Patent [19]

Maeda et al.

[11] Patent Number: 4,992,369
[45] Date of Patent: Feb. 12, 1991

[54] FERMENTATION PROCESS FOR GLYCOPEPTIDE ANTIBIOTIC

[75] Inventors: Hiroshi Maeda; Junsuke Tone, both of Chita, Japan; John C. Ruddock, Ash; Kelvin S. Holdom, Minster, both of England

[73] Assignee: Pfizer Inc., New York, N.Y.

[21] Appl. No.: 366,576

[22] Filed: Jun. 15, 1989

Related U.S. Application Data

[62] Division of Ser. No. 101,626, Sep. 28, 1987, abandoned.

[30] Foreign Application Priority Data

Oct. 16, 1986 [GB] United Kingdom ............... 8624806

[51] Int. Cl.$^5$ .................. C12P 17/18; C12N 1/20; A61K 37/02
[52] U.S. Cl. ................... 435/119; 35/252.6; 35/827; 514/8
[58] Field of Search ............ 435/827, 119, 252.6

[56] References Cited

U.S. PATENT DOCUMENTS

| | | | |
|---|---|---|---|
| 3,923,980 | 12/1975 | Hamill et al. | 435/827 |
| 4,038,383 | 7/1977 | Celmer et al. | 435/827 |
| 4,100,273 | 7/1978 | Pagani et al. | 435/827 |
| 4,169,887 | 10/1979 | Celmer et al. | 435/827 |
| 4,280,001 | 7/1981 | Pagani et al. | 435/827 |
| 4,328,316 | 5/1987 | Cavalleri et al. | 435/252.6 |
| 4,462,942 | 7/1984 | Hamill et al. | 260/112.5 R |
| 4,504,467 | 3/1985 | Molloy et al. | 424/118 |
| 4,587,218 | 5/1986 | Hershberger | 435/252.6 |

OTHER PUBLICATIONS

Barna et al., *Ann. Rev. Microbiol.* 1984, 38:339–57.

*Primary Examiner*—Jacqueline Stone
*Assistant Examiner*—Marian C. Knode
*Attorney, Agent, or Firm*—Peter C. Richardson; J. Trevor Lumb; Robert K. Blackwood

[57] ABSTRACT

A new glycopeptide antibiotic UK-68,597 can be prepared by submerged aerobic propagation in aqueous nutrient media of Actinoplanes sp. ATCC 53533. The antibiotic and its cationic salts are active against a variety of microorganisms and are effective in controlling coccidiosis, enteritis, swine dysentery and theileriosis as well as being effective in promotion of growth and/or improving efficiency of feed utilization in poultry, swine and ruminants.

5 Claims, No Drawings

FERMENTATION PROCESS FOR GLYCOPEPTIDE ANTIBIOTIC

This is a division of application Ser. No. 07/101,626, filed on Sept. 28, 1987 now abandoned.

BACKGROUND OF THE INVENTION

This invention is concerned with a new member of the glycopeptide group of antibiotics, a class of compounds characterized biologically by their Gram-positive antibacterial action exerted by the inhibition of bacterial cell wall biosynthesis. This family of antibiotics includes such well known agents as avoparcin; actaplanin; teichoplanin; A41030 complex and the aridicins. The subject has been reviewed by Williams and Barna. "Structure and mode of action of glycopeptide antibiotics of the vancomycin group". *Annual Rev. Microbiol.*, 38, 339, 1984.

In the search for new antibiotics, structural modification of known antibiotics is attempted whenever possible. This approach is limited, however, to modifications which retain the desired activity. Many antibiotics, including the glycopeptides, have such complex structures that even small changes can be difficult to make by chemical means. The discovery of new antibiotics produced by fermentation processes continues, therefore, to be of great importance even in cases where the antibiotic, once recognized, is quite similar to a previously known antibiotic.

The glycopeptide antibiotics listed above are active against Gram-positive bacteria. They have therefore been employed with varying degrees of success for administration to poultry and other farm animals, including the ruminants and pigs, to control infection or to promote growth or milk production.

Among a number of conditions which can be treated with these agents is enteritis, a disease which can cause severe economic losses to livestock producers. Enteritis occurs in chickens, swine, cattle and sheep and is attributed mainly to anaerobic bacteria, particularly *Clostridium perfringens*, and viruses. Enterotoxemia in ruminants, an example of which is "overeating disease" in sheep, is a condition caused by *C. perfringens* infection.

Performance enhancement (increased rate of growth and/or increased efficiency of feed utilization) in ruminants such as cattle, and in monogastric animals such as swine, is another economically desirable objective of veterinary science. Of particular interest is improved performance achieved by increasing the efficiency of feed-utilization. The mechanism for utilization of the major nutritive portion of ruminant feeds is well known. Microorganisms in the rumen of the animal degrade carbohydrates to produce monosaccharides and then convert these monosaccharides to pyruvate compounds. Pyruvates are metabolized by microbiological processes to form acetates, butyrates or propionates, collectively known as volatile fatty acids. Although acetates and butyrates are utilized, propionates are utilized with greater efficiency. Furthermore, when too little propionate is available, animals may develop ketosis. A beneficial compound, therefore, stimulates animals to produce a higher proportion of propionates from carbohydrates, thereby increasing carbohydrate utilization efficiency and also reducing the incidence of ketosis.

DETAILED DESCRIPTION OF THE INVENTION

This invention is concerned with a new acidic glycopeptide antibiotic, designated UK-68,597, produced by the submerged aerobic propagation in aqueous nutrient media of a microorganism isolated from a soil sample from San Diego, California, USA. The antibiotic is active against a variety of microorganisms and is effective in promoting growth and increasing efficiency of feed utilization in poultry, swine and ruminants.

The microorganism is designated herein as Actinoplanes sp., ATCC 53533. It was recognized to be a species of Actinoplanes because of its narrow hyphae, yellowish-orange to orange substrate mycelium and whole-cell amino acid and sugar compositions.

A culture thereof, designated herein as N693-3 was planted from a slant onto ATCC no. 172 broth and grown for four days at 28° C. on a shaker. It was then centrifuged for 20 minutes, washed three times with sterile distilled water and planted on media commonly used for identification of members of the Actinomycetales as hereinafter described. The culture was incubated at 28° C. and the results were read at varying times but most were commonly taken at 14 days. The colors are described in common terminology but exact colors were determined by comparisons with color chips from the Color Harmony Manual, fourth edition. The methods of whole-cell amino acid and sugar analyses are those described in Becker, B et al, *Appl. Microbiol.* 12,421–423, 1964; and in Lechevalier, M. P., *J. Lab. Clin. Med.*, 71,934–944, 1968.

Identification media used for the characterization of the culture and references for their composition are as follows:

1. Tryptone-Yeast Extract Broth—(ISP medium no. 1, Difco).
2. Yeast Extract-Malt Extract Agar—(ISP medium no. 2, Difco).
3. Oatmeal Agar—(ISP medium no. 3, Difco).
4. Inorganic Salts-Starch Agar—(ISP medium no. 4, Difco).
5. Glycerol-Asparagine Agar—(ISP medium no. 5, Difco).
6. Peptone-Yeast Extract Iron Agar—(ISP medium no. 6, Difco).
7. Czapek-Sucrose Agar—S. A. Waksman, The Actinomycetes, Vol. 2, medium no. 1, p. 328, 1961.
8. Glucose-Asparagine Agar—Ibid, medium no. 2, p. 328.
9. Bennett's Agar—Ibid, medium no. 30, p. 331.
10. Emerson's Agar—Ibid, medium no. 28, p. 331.
11. Nutrient Agar—Ibid, medium no. 14, p. 330.
12. Glucose-Yeast Extract Agar—Ibid, medium no. 29, p. 331.
13. Peptone-Czapek Agar—J. N. Couch, *J. Elisha Mitchell Soc.*, 79,53–70, 1963.
14. R. J. Hickey and Tresner's Agar—R. J. Hickey and H. D. Tresner, *J. Bacteriol.*, 64,891–892, 1952.
15. Gordon and Smith's Tyrosine Agar—R. E. Gordon and M. M. Smith, *J. Bact.*, 69,147–150, 1955.
16. Casein Agar—Ibid.
17. Calcium Malate Agar—S. A. Waksman, *Bact. Rev.*, 21,1–29, 1957.
18. Gelatin Agar—R. E. Gordon and J. M. Mihm, *J. Bact.*, 73,15–27, 1957.
19. Starch Agar—Ibid.
20. Organic Nitrate Broth—Ibid.

21. Potato Carrot Agar—M. P. Lechevalier, *J. Lab. and Clin. Med.* 71,934,944, 1968, but use only 30 g potatoes, 2.5 g carrots and 20 g agar.

22. 2% Tap Water Agar.

23. Dextrose Nitrate Broth—S. A. Waksman, The Actinomycetes, Vol. 2, medium no. 1, p. 328, 1961, with 3 g dextrose substituted for 30 g sucrose and agar omitted.

24. Cellulose Utilization
   (a) H. L. Jensen, *Proc. Linn. Soc. N.S.W.*, 55,231–248, 1930.
   (b) M. Levine and H. W. Schoenlein, A Compilation of Culture Media, medium no. 2511, 1930.

25. Skimmed Milk—Difco.

26. Carbohydrates—G. M. Luedemann and B. C. Brodsky, *Antimicrob. Agents Chemother.*, 1964,47, 1965, ISP medium no. 9, Difco.

27. Temperature Range—ATCC medium 172 in ATCC Media Handbook, 1st ed., p. 10, 1984.

The observations of growth and appearance of the organism were as follows:

Yeast Extract-Malt Extract Agar—Growth good, orange to yellowish orange (5ia, 5la, 4ga), wrinkled, raised, no aerial mycelium; reverse same as surface; no soluble pigment.

Oatmeal Agar—Growth moderate to good, cream but pale yellowish orange toward the edge, moderately raised, smooth, no aerial mycelium; reverse pale yellowish orange (3ca, 3ea); no soluble pigment.

Inorganic Salts-Starch Agar—Growth moderate, yellowish orange (4ea, 4ga), smooth, slightly raised, no aerial mycelium; reverse same as surface; no soluble pigment.

Glycerol-Asparagine Agar—Growth good, orange to dark orange (4la, 5la), wrinkled, raised, no aerial mycelium; reverse same as surface; no soluble pigment.

Czapek-Sucrose Agar—Growth moderate, pale yellowish orange (3ca), smooth, slightly raised, no aerial mycelium; reverse pale yellowish orange (3ca, 3ea); no soluble pigment.

Glucose-Asparagine Agar—Growth moderate to good, orange (4ga, 4ia), smooth but may be wrinkled toward the edge, moderately raised, no aerial mycelium; reverse orange (4ia, 4la); no soluble pigment.

Bennett's Agar—Growth good, yellowish orange (4ia, 4pa), wrinkled, raised, no aerial mycelium; reverse yellowish orange (4la, 4pa), no soluble pigment.

Emerson's Agar—Growth good, reddish orange (6ia, 6½ga), wrinkled, raised, no aerial mycelium; reverse same as surface; soluble pigment yellowish brown (4lc).

Nutrient Agar—Growth poor to moderate, reddish orange (5ea, 5ga, 6ga), smooth but wrinkled toward end of streak, thin but raised toward end of streak, no aerial mycelium; reverse same as surface; no soluble pigment.

Glucose-Yeast Extract Agar—Growth excellent, orange (4la, 5la), wrinkled, highly raised, no aerial mycelium; reverse same as surface; soluble pigment yellowish brown (3lc).

Peptone-Czapek Agar—Growth scant, yellowish orange (4ia), granular, raised, no aerial mycelium; reverse same as surface; no soluble pigment.

Hickey and Tresner's Agar—Growth good, yellowish to yellowish orange (3ea, 3ia, 4ia), wrinkled, raised, no aerial mycelium; reverse same as surface; no soluble pigment.

Gordon and Smith's Tyrosine Agar—Growth moderate, dark reddish (6le, 6½le), smooth but may be wrinked at end of streak, thin to slightly raised, no aerial mycelium; reverse brown to reddish brown (5le, 6la); soluble pigment dark brown (5ng).

Casein Agar—Growth moderate to good, bright orange (5na, 5pa), wrinkled, moderately raised, no aerial mycelium; reverse same as surface; soluble pigment yellowish (2lc).

Calcium Malate Agar—Growth poor to moderate, pale yellowish orange (3ea, 4ea), smooth, thin, no aerial mycelium; reverse same as surface; no soluble pigment.

Gelatin Agar—Growth moderate to good, orange (5ga, 5ia), wrinkled, moderately raised, no aerial mycelium; reverse same as surface; no soluble pigment.

Starch Agar—Growth good, orange (5ia), wrinkled, raised, no aerial mycelium; reverse orange (5ia, 6ga); no soluble pigment.

Potato Carrot Agar—Growth moderate, orange-yellow (3ea, 3ga), smooth, thin, no aerial mycelium; reverse same as surface; no soluble pigment.

Tap Water Agar—Growth poor to moderate, cream (2ca), smooth, thin, no aerial mycelium; reverse colorless to cream (2ca); no soluble pigment.

Morphological Properties—Vegetative hyphae narrow, straight or undulate, branched, 0.4–1.0 $\mu$m diam, no spores or sporangia were produced after four weeks of incubation on the media used; after seven weeks of incubation at either 21° C. or 28° C. on oatmeal agar, glycerol-asparagine agar, Czapek-sucrose agar, glucose-yeast extract agar or Hickey and Tresner's agar, no spores or sporangia were produced.

Biochemical Properties—Melanin not produced in tryptone-yeast extract broth; hydrogen sulfide produced on peptone-yeast extract iron agar; gelatin liquefied; starch hydrolyzed; nitrate reduced to nitrite in both organic nitrate broth and dextrose nitrate broth; good growth but no disintegration on both cellulose broths; coagulation and clearing on milk; casein digestion positive; digestion of calcium malate negative; digestion of tyrosine negative. Carbohydrate utilization; glucose, arabinose, fructose, inositol, mannitol, raffinose, rhamnose, sucrose, xylose, cellobiose, dulcitol, galactose, glycerol, lactose, mannose, melezitose, melibiose, ribose, salicin, soluble starch, sorbitol and trehalose utilized; adonitol and sorbose not utilized

TEMPERATURE RELATIONS

| 21° C. | 28° C. | 37° C. | 45° C. |
| --- | --- | --- | --- |
| Excellent Growth | Excellent Growth | Good to Excellent Growth | No Growth |

Cell Wall Analysis—The whole-cell hydrolysates contained 3-hydroxydiaminopimelic acid, xylose, arabinose, glucose, mannose and ribose.

The culture N693-3 is characterized by the yellowish-orange to orange substrate mycelium, the lack of spores or sporangia, and the lack of soluble pigments on most of the media used. Attempts to induce spore or sporangium production have failed. The negative reactions include melanin production, disintegration of cellulose, digestion of calcium malate or tyrosine, utilization of adonitol and sorbase, and growth at 45° C. The following reactions are positive: gelatin liquefaction, starch hydrolysis, nitrate reduction, growth on cellose, coagulation and clearing on milk, casein digestion; utilization of all the sugars used except for adonitol and sorbose; growth at 21° C., 28° C. and 37° C. The presence of 3-hydroxydiaminopimelic acid, xylose, arabinose, mannose and ribose indicates that the culture belongs in cell wall Type II.

Since the culture under study has not produced sporangia, and since speciation of the genus Actinoplanes depends on the size and shapes of sporangia, identification of it to the species level is impossible and hence the culture N693-3 is considered as a species of the genus Actinoplanes and designated Actinoplanes sp. It has been deposited at the American Type Culture Collection, 12301 Parklawn Drive, Rockville, Md. 20852, U.S.A. under the provisions of the Budapest Treaty on 3rd September, 1986 under the accession number ATCC 53533.

Cultivation and isolation of Antibiotic UK-68,597 may be conducted under conditions similar to those generally employed to produce antibiotics by fermentation. Cultivation preferably takes place in aqueous nutrient media under submerged aerobic conditions with agitation at a temperature of 24° to 36° C. Nutrient media useful for cultivation include a source of assimilable carbon such as sugars, starches and glycerol; a source of organic nitrogen such as casein, enzymatic digest of casein, soybean meal, cotton seed meal, peanut meal, wheat gluten, soy flour, meat meal and fish meal. A source of growth substances such as grain solubles, fish meal, cotton seed meal, and yeast extract as well as mineral salts such as sodium chloride and calcium carbonate and trace elements such as iron, magnesium, copper, zinc, cobalt and manganese may also be utilized with advantageous results. If excessive foaming is encountered during fermentation, antifoam agents such as polypropylene glycols or silicones may be added to the fermentation medium. Aeration of the medium in tanks for submerged growth is preferably maintained at the rate of about ½ to 2 volumes of sterile free air per volume of fermentation broth per minute forced into the broth through a sparger. Agitation may be maintained by means of agitators generally familiar to those skilled in the fermentation art. The rate of agitation depends on the type of agitator employed. A shake flask is usually run at 150 to 200 cycles per minute whereas a fermenter is usually run at 300 to 1700 revolutions per minute. Aseptic conditions must, of course, be maintained through the transfer of the organism and throughout its growth.

Inoculum for the preparation of the antibiotics according to this invention may be obtained by employing growth from a slant of the culture or Roux bottles inoculated with the culture. A solid medium suitable for initial growth of the organism on slants and in Roux bottles is ATCC medium no. 172. The growth may be used to inoculate either shake flasks or inoculum tanks or the inoculum tanks may be seeded from the shake flasks. Growth in shaken flasks will generally have reached its maximum in 4 to 5 days whereas inoculum in submerged inoculum tanks will usually be in the most favorable period in 3 to 6 days.

The progress of antibiotic production during fermentation and the bioactivity of the fermentation broth can be monitored by biological assay of the broth employing a sensitive strain of *Staphylococcus aureus* or *Bacillus subtilis*. *B. subtilis* ATCC 6633 is a suitable strain for this purpose. Standard plate assay technique is employed in which the zone of inhibition surrounding a filter paper disc saturated with the broth is used as a measure of antibiotic potency. Also, thin-layer chromatography employing silica gel is a useful tool for detecting the antibiotics produced in fermentation media and analyzing the composition of crude and purified materials extracted from the fermentation broths. The chromatograms are developed with acetonitrile, water, ammonium hydroxide (3:1:7) and the developed plate is overlayed with agar seeded with either *S. aureus* or *B. subtilis* and incubated at 37° C. for 16 hours to visualize the antibiotics.

Antibiotic UK-68,597 produced by fermentation of Actinoplanes sp, ATCC 53533 may be separated and removed by adjusting the pH of the whole broth to pH 10 and filtering the broth to remove mycelium. The antibiotic can be further purified by a series of adsorptions on suitable adsorbents, such as ion exchange resins, chemically modified hydrophobic inorganic supports as used in high performance reverse-phase liquid chromatography, or high porosity polymers, eluting the antibiotic in each case with a suitable solvent.

The antibiotic compound of this invention is acidic, and will form cationic salts by reaction with basic agents. All such salts are within the scope of this invention.

Antibiotic UK-68,597 can be characterized by virtue of the following physiochemical properties.

(A) Ultraviolet absorption spectrum. The compound exhibits the following absorption maxima:

| Solvent | λ max (nm) |
| --- | --- |
| (a) methanol | 238, 280, 370 |
| (b) methanol, 0.1 M HCl (9:1) | 238, 286 |
| (c) methanol, 0.1 M NaOH (9:1) | 264, 300, 358 |

(B) Infrared absorption spectrum. The compound exhibits the following absorption maxima (cm$^{-1}$): 3700–3100; 1660; 1595; 1500; 1230; 1140; 1055; 1015; 990; 755.

(C) Optical rotation $[\alpha]_D^{25} = -25.6°(c=0.1, DMSO)$ (D) Retention-time (Rt) of 12.4 minutes, when analyzed by reverse phase HPLC under the following conditions:

Column: C-18 Micro-Bondapack, 3.9 mm (i.d.)×150 mm (Waters)
Eluent: CH$_3$CN 10%, 0.1M aqueous ammonium formate 90%, adjusted to pH 7.4
Flow rate: 2 ml/min
Detection: U.V. at 225 nm (E) Molecular weight deduced from a fast atom bombardment mass spectrum showing the M+ peak at m/e 1651.

UK-68,597 is of the following structural formula:

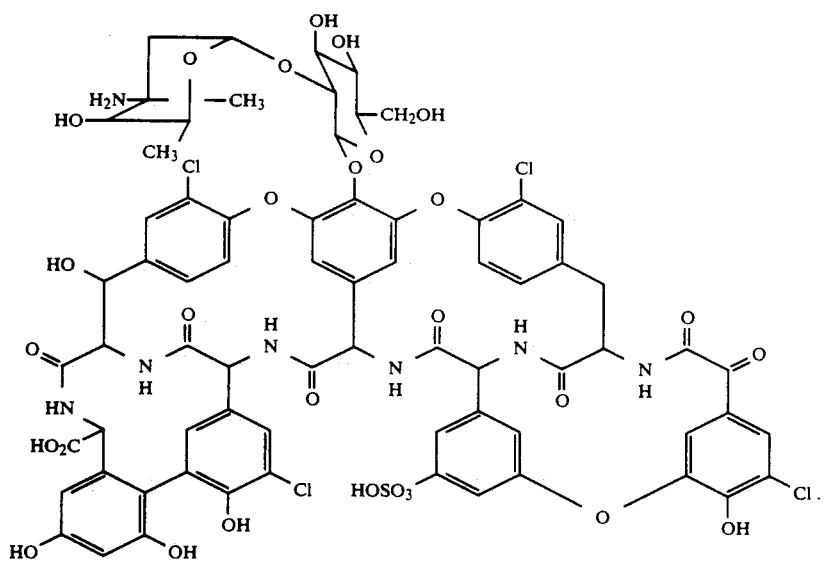

Antibiotic UK-68,597 exhibits inhibitory action against the growth of a number of Gram-positive microorganisms. In Table 1, below, the results of in vitro tests are summarized. For this test each organism is inoculated in a series of test tubes containing nutrient medium and varying concentrations of antibiotic UK-68,597 to determine the minimal concentration of the compound in mcg./ml. which inhibits the growth of the organism over a period of 24 hours (MIC).

TABLE I

ANTIBACTERIAL ACTIVITY

| Organism | Strain No. | MIC, mcg./ml. Antibiotic UK-68,597 |
|---|---|---|
| Staphylococcus aureus | 01A106 | 12.5 |
|  | 01A539 | 12.5 |
|  | 01A540 | 12.5 |
| Actinomyces pyogenes | 14D011 | <0.2 |
| Pasteurella multocida | 59A006 | >100 |
| Clostridium perfringens | 10A009 | <0.2 |
| Bacteroides fragilis | 78C024 | >100 |
| Fusobacterium necrophorum | 84C004 | >100 |
| Treponema hyodysenteriae | 94A007 | >100 |

Against the gram-negative bacteria such as *Escherischia coli*, and *Pseudomonas aeruginosa*, MIC values were >100 in each case.

The value of animal feeds has generally been determined directly by feeding the animal. British Patent Specification No. 1,197,826 details an in vitro rumen technique whereby the changes occurring in feeds brought about by microorganisms are measured more readily and with great accuracy in the evaluation of animal feeds. This technique involves the use of an apparatus in which the digestive processes of the animals are conducted and studied in vitro. The animal feeds, rumen inoculum and various growth promotants are introduced into and withdrawn from a laboratory unit under carefully controlled conditions and the changes taken place are studied critically and progressively during the consumption of the feed by the microorganisms. An increase in the propionic acid content of the rumen fluid indicates that a desirable response in overall ruminant performance has been brought about by the growth promotant in the feed composition. The change in propionic acid content is expressed as percent of the propionic acid content found in the control rumen fluid. Long term in vivo feeding studies are used to show a reliable correlation between propionic acid increase in the rumen fluid and improved animal performance.

Rumen fluid is collected from a fistulated cow which is fed on a commercial fattening ration plus hay. The rumen fluid is immediately filtered through cheese cloth, and 10 ml. added to a 50 ml. conical flask containing 400 mg. of standard substrate (68% corn starch+17% cellulose+15% extracted soybean meal), 10 ml. of a pH 6.8 buffer and the test compound. The flasks are gassed with oxygen free nitrogen for about two minutes, and incubated in a shaking water bath at 39° C. for about 16 hours. All tests are conducted in triplicate.

After incubation, 5 ml. of the sample is mixed with 1 ml. of 25% metaphosphoric acid. After 10 minutes 0.25 ml. of formic acid is added and the mixture centrifuged at 1500 rpm for 10 minutes. Samples are then analyzed by gas-liquid chromatography by the method of D. W. Kellog, *J. Dairy Science*, 52, 1690, 1969. Peak heights for acetic, propionic and butyric acids are determined for samples from untreated and treated incubation flasks.

When tested by this in vitro procedure, Antibiotic UK-68,597 at the level of 10 micrograms per milliliter gave rise to an increase of about 25% in the production of propionic acid over that produced in the control solution without added Antibiotic UK-68,597. By comparison the commercially available compound salinomycin (a polyether antibiotic) at 10 mcg/ml. produced about an 46% increase of propionic acid over the control.

These data shows that Antibiotic UK-68,597 will improve feed utilization by ruminants such as cattle and sheep. The compounds will also have a similar effect in monogastric animals such as pigs and poultry.

In particular, as shown in Table 2, Antibiotic UK-68,597 is of benefit for improving weight gain and feed utilization in poultry.

The compound was added to the feed which is provided to four day old broiler chicks housed in tier-brooders on a free-access basis. After ten days the birds are weighed and the live weight gain compared with an untreated control group to give a percentage improvement in live weight gain. The amount of feed consumed is divided by the live weight of the animals in the group at the completion of the trial to give a feed conversion ratio (which gives a measure of the amount of feed required to produce 1 kg increase in body weight), and this is also compared with the control group and the improvement in the feed conversion ratio calculated as a percentage. The results show a significant improvement in both live weight gain and in food conversion efficiency when Antibiotic UK-68,597 is added to feed at a level of 10 ppm:

TABLE 2
PERFORMANCE ENHANCEMENT ACTIVITY IN POULTRY

| Ppm | Liveweight gain (% improvement) | Food conversion ratio (% improvement) |
|---|---|---|
| 10 | 4.3 | 2.7 |

Antibiotic UK-68,597 may be incorporated in feed compositions as the free acid or as a salt. Alternatively crude forms of Antibiotic UK-68,597 or dried fermentation broth containing the antibiotics may be used by incorporation in feed compositions to give the desired potency concentrations of antibiotic.

The invention is further illustrated by the following Examples.

EXAMPLE 1

1. Preparation of Inoculum

A sterile aqueous medium having the following composition was prepared.

| Ingredient | Grams/liter |
|---|---|
| Glucose | 1 |
| Starch | 24 |
| Peptone | 5 |
| Yeast extract | 5 |
| Meat extract | 3 |
| Calcium carbonate | 4 |

One liter of medium is distributed into 2.8 liter conical flasks and sterilized at 120° C. and 15 p.s.i. for 30 minutes. After cooling, the medium is inoculated with a vegetative cell suspension from a slant culture of *Actinoplanes sp.* ATCC 53533

The flasks are shaken at 28° C. on a rotary shaker having a displacement of 4 to 7 cm and 150 to 200 cycles per minute for three to five days.

2. FERMENTATION AND ISOLATION OF ANTIBIOTIC UK-68,597

Fifty mls. of the inoculum medium described in Example 1 was used to inoculate each of nine five liter fermentation vessels containing 2.5 liters of sterile medium of the following composition to which 1 ml of polypropylene glycol antifoaming agent had been added:

| Ingredient | Grams/liter |
|---|---|
| Cerelose | 10.0 |
| Corn starch | 10.0 |
| Soya flour | 10.0 |
| Distillers solubles | 5.0 |
| Sodium chloride | 5.0 |

-continued

| Ingredient | Grams/liter |
|---|---|
| Calcium carbonate | 1.0 |
| Cobalt chloride | 0.002 |
| Water to 1 liter | |
| pH 6.9-7.0 | |

Fermentation was carried out at 28° C. with stirring at 1500 revolutions per minute and aeration at one volume air per volume of broth per minute until substantial activity was observed (based on antibiotic disc assay versus *B. subtilis* ATCC 6633), usually 4-6 days. The bioactivity of the broth, and of subsequent recovery streams, was followed by using a sensitive strain of *Bacillus subtilis* ATCC 6633 or *Staphylococcus aureus* ATCC 6538. The antibiotic component in the broth and recovery streams was detected after chromatographic separation using silica gel plates developed with acetonitrile, water, ammonium hydroxide(3:1:0.7). The plates were visualized with UV light at 254 nm and then overlayed with agar, seeded with either *S. aureus* or *B. subtilis*, to which 1.0 ml of a 1% solution of 2,3,5-triphenyl-2H-tetrazolium chloride had been added, and incubated at 37° C. for 16 hours to visualize the antibiotic as a white area against a pink background.

At the end of the fermentation production stage, the broth from all the fermenters was adjusted to pH 10 and filtered to remove mycelium. The antibiotic UK-68,597 was adsorbed onto an affinity column comprising a D-alanyl-D-alanine ligand immobilized on an agarose matrix (as described in EP 0132117), and eluted with a mixture of acetonitrile and 0.1N ammonium hydroxide (30:70). Further purification was achieved using high performance liquid chromatography using silanised silica gel as a support and acetonitrile, 0.1M aqueous ammonium formate (pH 7.3) (1:9) as eluent to give UK-68,597 in pure form.

EXAMPLE 2

Two liters of an inoculum prepared as described in Example 1 was used to inoculate 70 liters of inoculum medium having the composition as described in Example 1 contained in a 100 liter fermenter. This second stage inoculum was incubated at 28° C., with an agitation speed of 450 revolutions per minute and an air flow rate of one volume air per volume of broth per minute. After 48 hours incubation the inoculum was used to inoculate 1200 liters of medium of the following composition, contained in a 2000 liter fermenter:

| Fermentation Medium | |
|---|---|
| Ingredient | Grams/liter |
| Cerelose | 10 |
| Corn starch | 10 |
| Soya flour | 10 |
| Cobalt Chloride | 0.002 |
| Distillers solubles | 0.5 |
| Sodium chloride | 5 |
| Calcium carbonate | 1 |

The fermenter was maintained at 28° C., with aeration and stirring at 160 revolutions per minute. After 96 hours the pH of the whole broth was adjusted to pH 10.0, and filtered through a filter press pre-coated with filter aid. The solids containing the microorganism were discarded, and the filtrate adjusted to pH 7.0. The filtrate was passed down a column of Amberlite XAD-2 resin (Rohm & Haas), the column was washed with water and the Antibiotic UK-68,597 eluted with 50% aqueous acetone.

The eluate was concentrated to 12 liters. After dilution with 1.75 liters of 0.1M aqueous ammonium formate, 3.5 liters of this concentrate was charged onto a C-18 Prep-Pak column in a Waters Prep 500 high pressure liquid chromatography system. The column was eluted in turn with the following solvents:

| Solvent | (liter) Volume |
| --- | --- |
| 0.1 M aqueous ammonium formate | 3 |
| 0.1 M aqueous ammonium formate, acetonitrile (1:19) | 4.5 |
| 0.1 M aqueous ammonium formate, acetonitrile (1:9) | 1.3 |
| water | 0.9 |
| acetonitrile in water (3:7) | 5.5 |

The antibiotic rich fractions were concentrated and adsorbed onto Amberlite XAD-2 resin. Elution of the resin using 50% aqueous acetone, concentration of the relevant fractions and lyophilisation gave UK-68,597 in salt free form.

We claim:

1. A process for producing an antibiotic UK-68,597 which comprises cultivating a microorganism *Actinoplanes* sp. ATTC 53533 or a mutant or recombinant form thereof having the ability to produce said antibiotic in an aqueous culture medium containing an assimilable source of carbon, nitrogen and inorganic salts under submerged aerobic fermentation conditions until a substantial amount of said antibiotic is produced by said microorganism in said culture medium and then recovering said antibiotic UK-68,597.

2. A process according to claim 1 wherein said antibiotic is recovered as a mycelial preparation or by spray-drying of said culture medium in its entirety.

3. The process of claim 1 wherein the microorganism is Actinoplanes sp. ATCC 53533.

4. A biologically pure culture of a strain of a microorganism of the genus Actinoplanes having the identifying characteristics of Actinoplanes sp. ATCC 53533, or a mutant or recombinant form thereof, said culture being capable of producing the antibiotic UK-68,597, or a pharmaceutically acceptable cationic salt thereof, in recoverable quantity upon cultivation in an aqueous nutrient medium containing an assimilable source of carbon, nitrogen and inorganic salts.

5. A culture of claim 4 in freeze dried form.

* * * * *